(12) United States Patent
Brown

(10) Patent No.: US 8,541,360 B2
(45) Date of Patent: Sep. 24, 2013

(54) PARENTERAL FORMULATIONS COMPRISING SUGAR-BASED ESTERS AND ETHERS

(75) Inventor: Douglas L. Brown, Twinsburg, OH (US)

(73) Assignee: Ben Venue Laboratories, Inc., Bedford, OH (US)

( * ) Notice: Subject to any disclaimer, the term of this patent is extended or adjusted under 35 U.S.C. 154(b) by 360 days.

(21) Appl. No.: 12/619,785

(22) Filed: Nov. 17, 2009

(65) Prior Publication Data

US 2010/0125051 A1 May 20, 2010

Related U.S. Application Data

(60) Provisional application No. 61/116,008, filed on Nov. 19, 2008.

(51) Int. Cl.
*A61K 38/00* (2006.01)
*A61K 31/70* (2006.01)
*A01N 43/04* (2006.01)

(52) U.S. Cl.
USPC ............................................. 514/1.1; 514/23

(58) Field of Classification Search
None
See application file for complete search history.

(56) References Cited

U.S. PATENT DOCUMENTS

| | | | |
|---|---|---|---|
| 4,814,470 A | | 3/1989 | Colin et al. |
| 4,822,601 A | * | 4/1989 | Goode et al. .................... 424/59 |
| 4,956,171 A | * | 9/1990 | Chang ............................ 424/449 |
| 4,966,779 A | * | 10/1990 | Kirk ................................ 426/72 |
| 5,057,501 A | | 10/1991 | Thornfeldt |
| 5,403,858 A | | 4/1995 | Bastard et al. |
| 5,415,869 A | | 5/1995 | Straubinger et al. |
| 5,438,072 A | | 8/1995 | Bobee et al. |
| 5,670,536 A | | 9/1997 | Durr et al. |
| 5,698,582 A | | 12/1997 | Bastart et al. |
| 5,714,512 A | | 2/1998 | Bastart et al. |
| 5,750,561 A | | 5/1998 | Bastart et al. |
| 5,756,450 A | * | 5/1998 | Hahn et al. .................... 514/20.5 |
| 5,795,896 A | * | 8/1998 | Lofroth et al. ................ 514/256 |
| 5,929,027 A | * | 7/1999 | Takama et al. ............... 514/11.9 |
| 6,056,405 A | | 5/2000 | Heintz et al. |
| 6,071,952 A | | 6/2000 | Owens et al. |
| 6,096,331 A | | 8/2000 | Desai et al. |
| 6,274,609 B1 | | 8/2001 | Yasueda et al. |
| 6,440,980 B1 | | 8/2002 | Marcelletti et al. |
| 6,610,317 B2 | | 8/2003 | Straub et al. |
| 6,638,537 B2 | | 10/2003 | Dennis et al. |
| 6,780,324 B2 | | 8/2004 | Le Garrec et al. |
| 6,919,370 B2 | | 7/2005 | Chen |
| 6,979,456 B1 | | 12/2005 | Parikh et al. |
| 7,871,977 B2 | * | 1/2011 | Rischer et al. ................. 514/9.8 |
| 2002/0077372 A1 | | 6/2002 | Gers-Barlag et al. |
| 2003/0158249 A1 | | 8/2003 | Chi et al. |
| 2005/0085759 A1 | * | 4/2005 | Dwight ............................ 604/2 |
| 2005/0175690 A1 | | 8/2005 | Edgren et al. |
| 2006/0188566 A1 | | 8/2006 | Liversidge et al. |
| 2006/0241170 A1 | | 10/2006 | Soon-Shiong et al. |
| 2007/0032438 A1 | | 2/2007 | Hu et al. |
| 2007/0082838 A1 | | 4/2007 | De et al. |

OTHER PUBLICATIONS

Sodium stearoyl-2-lactylate, prepared at the 46th JECFA (1996), published in FNP 52 Add 4 (1996). Accessed online on Feb. 29, 2012 at http://www.fao.org/ag/agn/jecfa-additives/specs/Monograph1/Additive-424.pdf, 4 pages.*
Prednisolone. The Elephant Formulary. Accessed online on Feb. 29, 2012 at http://www.elephantcare.org/Drugs/predniso.htm, 3 pages.*
Ahsan et al. Sucrose cocoate, a component of cosmetic preparations, enhances nasal and ocular peptide absorption. Int J Pharmaceutics, 2003, vol. 251, pp. 195-203.*
NIOSH List of Antineoplastic and Other Hazardous Drugs in Healthcare Settings 2012. Department of Health and Human Services. CDC. NIOSH. 2012. Accessed online Jul. 12, 2012 at http://www.cdc.gov/niosh/docs/2012-150/pdfs/2012-150.pdf. 20 pages.*
Lamson et al. The Anticancer Effects of Vitamin K. Review. Alternative Medicine Review, 2003. vol. 8, No. 3, pp. 303-318.*
Chowdury et al. Studies on the Fatty Acid Composition of Edible Oil. Bangladesh J. Sci. Ind. Res. 2007, vol. 42, No. 3, pp. 311-316.*
SRC PhysProp CAS 033125-97-2 (1996), accessed at http://www.syres.com/what-we-do/databaseforms.aspx?id=386 on Jan. 17, 2013, 1 page.*
SRC PhysProp CAS 114977-28-5 (1996), accessed at http://www.syres.com/what-we-do/databaseforms.aspx?id=386 on Jan. 17, 2013, 1 page.*

* cited by examiner

*Primary Examiner* — Marcela M Cordero Garcia
(74) *Attorney, Agent, or Firm* — Pearne & Gordon LLP

(57) ABSTRACT

The present invention relates to formulations for the parenteral administration of therapeutic agents, which contain sugar-based esters and ethers of fatty acids and fatty alcohols as surfactants. The formulations are advantageous for therapeutic agents which are insoluble or poorly soluble in water, and for reducing toxicity associated with common surfactants used in pharmaceutical formulations.

10 Claims, No Drawings

PARENTERAL FORMULATIONS COMPRISING SUGAR-BASED ESTERS AND ETHERS

CROSS REFERENCE TO RELATED APPLICATIONS

The present invention claims priority to U.S. Provisional Patent Application No. 61/116,008, filed Nov. 19, 2008, which is incorporated herein by reference in its entirety.

FIELD OF THE INVENTION

The present invention relates to improved parenteral formulations having sugar-based esters and ethers of fatty acids and fatty alcohols as surfactants. In particular, the invention relates to a new formulation of docetaxel containing sugar-based esters or ethers as surfactants, for parenteral administration, including the preparation and use thereof.

BACKGROUND

Many common pharmaceutical agents including many antibiotics, steroids, and certain vitamins are lipophilic, and poorly soluble (if at all) in water. This poor solubility creates difficulties in therapeutic administration, particularly parenteral administration, because bioavailability may be low and highly variable from patient-to-patient, high doses or numerous dosage units may be required per dose, there can be a slow onset of action, and performance is inconsistent. To solve these problems, efforts have been made to enhance solubility of insoluble pharmaceutical agents, for example by creating emulsions, encapsulating agents in liposomes or vesicles, and using surfactant micelles, but many of these efforts require complicated processing steps.

Common surfactants for drug solubilization include sodium lauryl sulfate, sodium sulphosuccinate, monodecyl trimethyl ammonium bromide, polysorbates, polyethylene glycols, and the like. However, many of these commonly used surfactants have toxic side effects such as hemolysis, damage to membrane permeability, changes to protein conformation, alteration of bioactivity of other compounds, and the like. Anionic and cationic surfactants are generally more toxic than non-ionic surfactants such as the polysorbate surfactants. Although polysorbates may have a better profile than an anionic or cationic surfactant they can still exhibit significant side effects upon administration. These side effects are enhanced by the non-degradable nature of some surfactants. Thus, difficulties exist in developing safe parenteral formulations of poorly soluble and insoluble therapeutic agents.

For example, docetaxel is a poorly soluble anticancer drug that is supplied in the non-ionic surfactant polysorbate 80 (Tween® 80). For administration, the docetaxel-polysorbate 80 is diluted with a mixture of aqueous ethanol, and then into a saline or dextrose solution. Adding the aqueous ethanol to the polysorbate containing the docetaxel requires strong mixing to ensure complete dissolution of the polysorbate, thereby creating substantial amounts of foam that does not subside for long periods of time, e.g., more than 30 minutes, which can be inconvenient for direct administration or preparation of an administrative solution. In addition to these administrative difficulties, the polysorbate 80 has been found to cause hypersensitivity reactions and cumulative fluid retention in patients administered docetaxel.

Therefore, there is a need for more satisfactory surfactants, particularly surfactants having reduced side effects, to enhance the delivery of water-insoluble drugs.

SUMMARY

Embodiments of the invention provide a pharmaceutical composition for parenteral administration comprising a therapeutic agent and a sugar-based surfactant selected from the group consisting of sugar fatty acid esters, sugar fatty alcohol esters, and sugar fatty alcohol ethers. In one aspect, the therapeutic agent may be poorly soluble in water, and may be selected from the group consisting of taxanes, anaesthetics, steroids, and antibiotics. In another aspect, the sugar-based surfactant is a mixture of $C_8$ to $C_{18}$ fatty components, and preferably is sucrose cocoate. The pharmaceutical compositions may also comprise excipients, such as preservatives and bulking agents. Methods of producing the pharmaceutical compositions, as well as methods of treating various diseases and disorders, are also provided.

The above and still further features and advantages of the present invention will become apparent upon consideration of the following detailed description of specific embodiments thereof, particularly when taken in conjunction with the accompanying drawings.

DETAILED DESCRIPTION

Reference will now be made in detail to the presently preferred embodiments of the invention, which, together with the following examples, serve to explain the principles of the invention. These embodiments are described in sufficient detail to enable those skilled in the art to practice the invention, and it is to be understood that other embodiments may be utilized, and that structural, physical, and chemical changes may be made without departing from the spirit and scope of the present invention. Unless otherwise defined, all technical and scientific terms used herein have the same meaning as commonly understood by one of ordinary skill in the art to which this invention belongs. Although any methods and materials similar or equivalent to those described herein can be used in the practice or testing of the present invention, the preferred methods, devices, and materials are now described.

The present invention relates to novel formulations for the parenteral formulation of therapeutic agents, particularly therapeutic agents that are insoluble or poorly soluble in water, such as docetaxel, propofol, etoposide, paclitaxel, and the like. The formulations comprise a therapeutic agent and a sugar-based ester or ether as a surfactant, which provides for improved solubility and reduced toxicity. The sugar-based esters can be sugar acid esters of fatty alcohols, or sugar alcohol esters of fatty acids, and the sugar-based ethers can be sugar alcohol ethers of fatty alcohols.

DEFINITIONS

Terms not specifically defined herein should be given the meanings that would be given to them by one of skill in the art in light of the disclosure and the context. For example, "sugar" is used herein to mean a saccharide, preferably a mono-, di-, or short chain oligo-saccharide. Other more specific definitions are as follows:

The term "bulking agents" comprise agents that provide the structure of a freeze-dried product. Common examples used for bulking agents include mannitol, glycine, lactose, sucrose, povidone K-17, carboxymethylcellulose, dextran, polyethylene glycol (PEG) 400/3350, poloxamers (e.g., Poloxamer 188), and the like. In addition to providing a pharmaceutically elegant cake, bulking agents may also impart useful qualities in regard to modifying collapse temperature, providing freeze-thaw protection, and enhancing stability over long-term storage. These agents can also serve as tonicity modifiers.

The term "isotonic" means that the formulation of interest has essentially the same osmotic pressure as human blood. Isotonic formulations will generally have an osmotic pressure from about 270-330 mOsm. Slightly hypotonic pressure is 250-269 and slightly hypertonic pressure is 331-350 mOsm. Osmotic pressure can be measured, for example, using a vapor pressure or ice-freezing type osmometer.

The terms "lyophilization," "lyophilized," and "freeze-dried" refer to a process by which the material to be dried is first frozen and then the ice or frozen solvent is removed by sublimation in a vacuum environment. An excipient may be included in pre-lyophilized formulations to enhance stability of the lyophilized product upon storage.

The term "pharmaceutical formulation" refers to preparations which are in such form as to permit the active ingredients to be effective, and which contains no additional components which are toxic to the subjects to which the formulation would be administered.

"Pharmaceutically acceptable" excipients (vehicles, additives) are those which can reasonably be administered to a subject mammal to provide an effective dose of the active ingredient employed.

The term "pharmaceutically acceptable salt," as used herein, includes those salts that retain the biological effectiveness and properties of the therapeutic agent and are not otherwise unacceptable for pharmaceutical use. Pharmaceutically acceptable salts include salts of acidic or basic groups, which groups may be present in the therapeutic agents. Those therapeutic agents that are basic in nature are capable of forming a wide variety of salts with various inorganic and organic acids. Pharmaceutically acceptable acid addition salts of basic therapeutics suitable for use herein are those that form non-toxic acid addition salts, i.e., salts comprising pharmacologically acceptable anions, such as the hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Therapeutic agents that include an amino moiety may form pharmaceutically acceptable salts with various amino acids, in addition to the acids mentioned above. Suitable base salts can be formed from bases which form non-toxic salts, for example, aluminium, calcium, lithium, magnesium, potassium, sodium, zinc and diethanolamine salts. See, e.g., Berge et al. (1977) J. Pharm. Sci. 66:1-19.

"Reconstitution time" is the time that is required to rehydrate a lyophilized formulation with a solution to a particle-free clarified solution.

A "stable" formulation is one in which the therapeutic agent therein essentially retains its physical stability and/or chemical stability and/or biological activity upon storage. Various analytical techniques for measuring protein stability are available in the art and are reviewed in Peptide and Protein Drug Delivery, 247-301, Vincent Lee Ed., Marcel Dekker, Inc., New York, N.Y., Pubs. (1991) and Jones, A. Adv. Drug Delivery Rev. 10:29-90 (1993). Stability can be measured at a selected temperature for a selected time period.

"Sugar ester" as used herein means "sugar alcohol fatty acid ester" or "sugar acid fatty alcohol ester" and "sugar ether" as used herein means "sugar alcohol fatty alcohol ether".

Sugar-Based Esters and Ethers

The sugar-based esters and ethers of the present invention are those which are suitable for use as surfactants. The sugar-based esters and ethers can be esters or ethers of (a) a sugar, a sugar alcohol, or a sugar derivative and (b) a fatty acid or fatty alcohol. In some formulations, esters may be preferred over ethers, and vice-versa, as will be evident to those skilled in the art. For example, although the surfactant properties of sugar esters and sugar ethers are generally similar, sugar ethers are typically more stable in alkaline conditions, which can be advantageous in certain fox mulations. These sugar-based esters and ethers are advantageous over commonly used surfactants for parenteral formulations, because they are non-toxic and are comprised of naturally occurring components found in the body as well as in common food sources. Thus, side effects from these sugar-based esters and ethers are minimized in comparison with surfactants such as the polysorbates.

The esters and ethers of the present invention may be formed by the combination of a sugar, sugar alcohol, or sugar derivative with a fatty acid, or by the combination of a sugar, sugar alcohol, or sugar derivative with a fatty alcohol. For example, a sucrose laurate ester may be formed by the combination of sucrose with lauric acid or lauryl sucronic acid ester, and unless otherwise specified herein, it is not necessary to the present embodiments that a particular ester (or ether) is the result of esterification (or etherification) with a fatty acid as opposed to a fatty alcohol, or vice-versa.

Preferred sugars employed in the preparation of the esters and ethers include monosaccharides, disaccharides and oligosaccharides known in the art, and in a preferred embodiment, the sugar is a mono-, di-, or tri-saccharide, or a mixture thereof. Exemplary sugars include allose, altrose, arabinose, cellobiose, erythrose, erythrulose, fructose, fucose, galactose, gentiobiose, glucose, gulose, idose, isomaltose, lactose, lactulose, lyxose, maltose, maltotriose, mannobiose, mannose, melezitose, raffinose, rhamnose, ribose, ribulose, sorbose, sucrose, talose, threose, trehalose, xylobiose, xylose and xylulose. In a preferred embodiment, the sugar is sucrose. Exemplary sugar alcohols include allitol, arabitol, ducitol, erythritol, galactitol, glycerol, glycol, iditol, inositol, isomalt, lactitol, mallitol, maltitol, mannitol, sorbitol, and xylitol. Exemplary sugar derivatives such as sulfonated sugars and sugar amines can also be used in the present embodiments. These examples are non-limiting examples, and it should be understood that any saccharide, sugar alcohol, or other sugar derivative that will provide a hydrophilic head group to the ester or ether and is otherwise pharmaceutically acceptable is suitable for use in the present embodiments.

The fatty acids and fatty alcohols used in the esters and ethers may be any fatty acid or fatty acid alcohol capable of providing a hydrophobic tail group such that the ester or ether can exert surface active properties. The fatty acids and fatty alcohols can be short chain (i.e., less than 8 carbons in length), medium chain (i.e., 8 to 14 carbons in length), or long chain (i.e., more than 14 carbons in length). Branched or unbranched fatty acids and fatty alcohols can be used. Non-limiting examples of suitable saturated fatty acids include butyric, caproic, caprylic, capric, lauric, myristic, palmitic, stearic, arachidic, and behenic acids, and non-limiting examples of suitable unsaturated fatty acids include myristoleic, palmitoleic, oleic, linoleic, linolenic, arachidonic, eicosapentaenoic, erucic, and docosahexaenoic acids. Non-limiting examples of suitable linear fatty alcohols include caproyl(caproic), caprylic, capric, lauryl, myristyl, palmityl (cetyl), palmitoleyl, stearyl, oleyl, linoleyl, linolenyl, arachidyl, behenyl, erucyl and lignoceryl alcohols, and non-limiting examples of suitable branched fatty alcohols include isocetyl, isostearyl, and isobehenyl alcohols.

In a preferred embodiment, the fatty component of the sugar-based ester or ether is a $C_{12}$ fatty component (e.g., lauric acid or lauryl alcohol), or a $C_8$ to $C_{18}$ fatty component. In a different embodiment, a mixture of medium and long chain fatty components are preferred, particularly a mixture of saturated and unsaturated $C_8$ to $C_{18}$ fatty components. In yet another embodiment, a mixture of saturated and unsaturated $C_8$ to $C_{18}$ fatty acids containing predominately lauric acid is preferred. In a different embodiment, the sugar-based ester or ether is a di- or tri-ester of a fatty acid or alcohol, or a di- or tri-ether of a fatty alcohol.

The sugar-based esters and ethers can be monoesters or monoethers, or can be di-, tri-, or poly-esters and ethers, depending on the sugar or sugar alcohol selected for use. In an embodiment, mono- and di-esters, or mono- and di-ethers are preferred. The esterification and etherification may occur at any free hydroxyl group in the sugar or sugar alcohol. For example, a typical di-saccharide used to prepare the sugar esters and ethers employed herein is sucrose, which has the formula I:

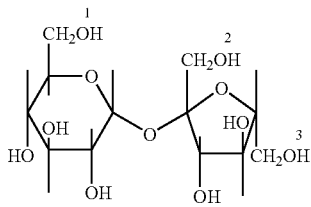

I

When sucrose is combined with an esterification agent in a 1:1 mole ratio, sucrose monoesters are formed predominantly. When the ratio of esterification agent to sucrose is 2:1, or greater, the di-, tri-, etc., esters are formed, up to a maximum of the octa-ester. Thus, sucrose monostearate, a typical sucrose fatty acid monoester, is esterified at one hydroxyl group, for example as shown in formula II:

While it is not important for the purposes of this invention, the sucrose monostearate is believed to be esterified predominantly at the hydroxyl group labelled (1) in the above formula I. However, commercial grades of this material include, as minor components, compounds wherein the sucrose is esterified at hydroxyl groups (2) and (3) as well as even smaller amounts esterified at one or more of the other five ring hydroxyl groups. A similar situation occurs with the other sugar-based esters used herein. For example, raffinose, which can be considered to be a condensate of galactose and sucrose, can be esterified in the foregoing manner in any one of its ten hydroxyl groups and used herein. However, it is believed that the esterification of raffinose occurs predominantly at the —$CH_2OH$ group on the galactose ring, with minor amounts of esterification also occurring at the —$CH_2OH$ groups on the sucrose portion of the molecule. Such variation in ester (and ether) location is expected, and unless otherwise specified it is not necessary to the present embodiments that the ester or ether bond location occur at a particular hydroxyl group.

Mixtures of esters or ethers are also contemplated for use in the present formulations. The mixtures may be varied in a number of ways. For example, a particular ester used in a formulation, such as a sugar monolaurate, may comprise a variety of sugar monolaurate esters, each esterified at a different hydroxyl group. Or, for example, a sugar laurate may comprise a variety of esters with varying degrees of esterification, for example a monolaurate, a dilaurate, a trilaurate, etc. Or, in yet another example, a sugar mono acid or sugar diacid may comprise mono- or di-esterification with lauryl alcohol fatty component. In still another example, a mixture containing a particular ester such as a sugar laurate may contain predominantly esters of lauric acid (or lauryl alcohol), but also contain esters of other fatty components, such as, e.g., esters of myristic acid (or myristyl alcohol). In yet another example, an "ester" may already be a mixture of fatty acids to form the esters, for example the "ester" sucrose cocoate is actually a mixture of esters including the laurate, palmitic, myristic, stearic and caproic esters of sucrose with smaller quantities of other short and long chain fatty acids as

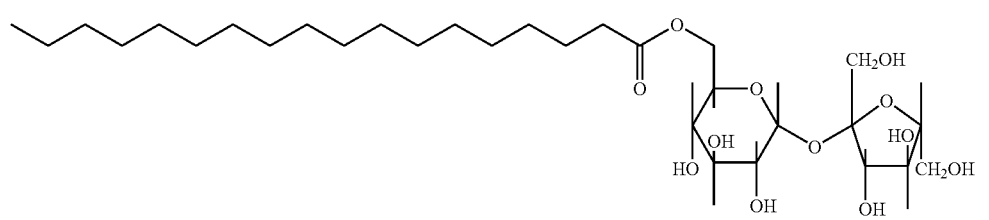

II and sucrose distearate, a typical sucrose fatty acid diester, is esterified at two hydroxyl groups, for example as shown in formula III:

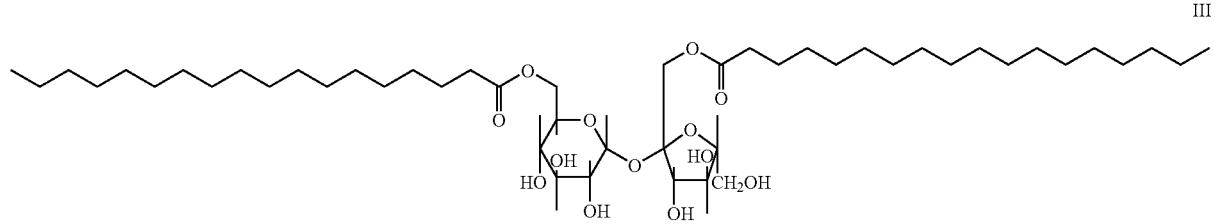

III well as mixed di- and tri-esters. These non-limiting examples of mixtures apply equally to sugar-based ethers as well as esters.

It is preferred that the sugar-based esters and ethers useful as surfactants in the embodiments of the present invention are amphiphilic and have a hydrophilic-lipophilic balance ("HLB") value that is preferably at least about half the sum of the HLB values of all other components of the formulation. More preferably, the surfactant has an HLB value that is from about half to about twice the sum of the HLB values of all other components of the formulation. More preferably, the surfactant has an HLB value that is about the same as the HLB value of all other components of the formulation. HLB values are readily available for surfactants, oils and carrier solutions or, if necessary, can be determined through routine experimentation as known in the art. Amphiphilic surfactants useful in the adjuvant of the invention have HLB values from about 2 to about 20, preferably from about 3 to about 17, and more preferably from about 4 to about 16.

The sugar-based esters and ethers may be prepared by any suitable means known in the art, for example by incubating an aqueous mixture of a sugar or sugar-alcohol, a fatty acid and a catalytically active amount of a lipolytic enzyme, and recovering the resulting ester from the mixture. Other methods include admixing the sugar with a fatty acid chloride at about 80° C., with simple removal of the hydrogen chloride formed and recovery of the sugar fatty acid ester. Similarly, a mixture of a methyl fatty acid ester and sugar can be heated at a temperature of about 90° C. in the presence of a base catalyst, distilling the methanol formed and recovering the sugar fatty acid ester. Many suitable esters and ethers are also commercially available.

Formulations

The parenteral formulation contain therapeutic agents and sugar-based esters or ethers as surfactants. In a preferred embodiment, a pharmaceutical composition for parenteral administration comprises a therapeutic agent and a sugar-based surfactant selected from the group consisting of sugar fatty acid esters, sugar fatty alcohol esters, and sugar fatty alcohol ethers. The physical and chemical characteristics of the formulations may be modified or optimized according to the skill in the art. Thus, pH, osmotic pressure, viscosity, and the content of various additional components may be chosen from any appropriate range known or modified from the examples given here.

The term "therapeutic agent" refers to any pharmaceutically acceptable acid, salt, ester, derivative, stereoisomer, pro-drug, or mixture of stereoisomers of a therapeutic agent, or to the therapeutic agent itself. The therapeutic agents used in the present formulations include agents for therapeutic, prophylactic, and diagnostic purposes. Therapeutic agents include, but are not limited to, analgesics, anaesthetics, anti-allergic agents, anti-angiogenics, anti-inflammatories including steroidal and non-steroidal anti-inflammatories (NSAIDs), anti-psychotics, anti-spasmodics, anti-ulcer, antibiotics, antibodies, anticonvulsants, antiemetics, antifungals, antihistamines, antineoplastics, antivirals, bronchodilators, cardiovascular agents, corticosteroids, diuretics, DNA binding (minor groove) compounds, hormones, immunosuppressive agents, mydriatics, metalloproteinase inhibitors, nucleic acids, oncological agents, plasmids, peptides, polypeptides and peptide-like therapeutic agents, proteins, receptor antagonists, respiratory stimulants, RNA aptamers, siRNAs, tissue inhibitors of metalloproteinases (TIMPs), vaccines, vascular endothelial growth factor (VEGF) inhibitors or antagonists or intraceptors, vitamins, as well as diagnostic agents such as dyes, contrast agents, fluorescent agents, radioisotopes (e.g., $P^{32}$, $Tc^{99}$, $I^{131}$, etc.) and the like that are useful in prevention, diagnosis and treatment of diseases, conditions, syndromes, and symptoms thereof.

In a preferred embodiment, the therapeutic agents are poorly soluble or insoluble in water, and in a different preferred embodiment, the therapeutic agent is poorly soluble in water and is selected from the group consisting of taxanes, anaesthetics, steroids, and antibiotics. In another embodiment, the therapeutic agent is a taxane (e.g., docetaxel, paclitaxel, etc.). In a different embodiment, the therapeutic agent is an anaesthetic (e.g., etomidate, lorazepam, propofol, etc.). In yet another embodiment, the therapeutic agent is an antineoplastic (e.g., etoposide, camptothecin, etc.). In still another embodiment, the therapeutic agent is a steroid (e.g., prednisolone, etc.). In a further embodiment, the therapeutic agent is an antibiotic (e.g., cyclosporine, doxorubicin, cephalexin, etc.). Hydrophobic therapeutic agents of particular interest include, but are not limited to, agents selected from the group consisting of docetaxel, doxorubicin, paclitaxel, propofol, etoposide, cyclosporine, and steroids. In a preferred embodiment, the therapeutic agent is a taxane comprising paclitaxel, docetaxel, or a derivative or analog thereof, and preferably is docetaxel.

The concentration of the sugar-based ester or ether surfactant in the formulation is dependent on different factors. For example, the higher the concentration of therapeutic agent or oil in the formulation, the more surfactant is required. Another factor that is useful to determine the concentration of a surfactant is the presence and concentration of other surfactants or surfactant-like agents, such as lecithins, in the formulation. The higher the concentration of a lecithin in the formulation, the less surfactant may be required.

The parenteral formulations may optionally also contain other conventional excipients and carriers such as for example anti-oxidants, bacteriostats, buffers, bulking agents, preservatives, release-modifiers, solutes, stabilizers, and tonicity modifiers, or combinations thereof. The formulations may be preserved by adding substances such as benzyl alcohol, parabens, phenols, or metabisulfite, and the tonicity may be modified by adding substances such as salts (NaCl, KCl, $MgCl_2$, $CaCl_2$, etc.) or bulking agents such as sucrose, mannitol, glycine, dextrans, etc. In a preferred embodiment, the formulations comprise mannitol as a bulking agent. In another preferred embodiment, the formulations comprise a poloxamer, preferably Poloxamer 188, as a bulking agent.

The formulation may contain solvents or co-solvents such as ethanol or 1,2-propanediol. Suitable pharmaceutically acceptable carriers for parenteral administration include a sterile liquid or mixture of liquids, including water, saline (e.g., normal saline (NS)), aqueous dextrose and related sugar solutions (e.g., five percent dextrose in water (D5W)), an alcohol, such as ethanol, isopropanol, 1,2-propanediol, or hexadecyl alcohol, an oil, and the like.

The formulations may be presented in unit-dose or multi-dose containers, for example sealed ampoules and vials, and may be stored in a freeze dried (lyophilized) condition. For example, a lyophilized therapeutic agent may be presented in a two-vial system, with one vial containing the lyophilized therapeutic agent (and optionally other components such as a bulking agent), and the other vial containing a diluent solution including the surfactant. Such a two-vial system requires reconstituting the therapeutic agent with the diluent containing the surfactant, and then adding a sterile liquid carrier, for example, Water for Injection (WFI), normal saline, or D5W, prior to use. Examples of therapeutic agents for which such a system may be preferred include the taxanes, such as paclitaxel and docetaxel.

In some cases, dilution into an administrative solvent such as normal saline, dextrose, etc., is unnecessary for administration. For example, a therapeutic agent may be presented in a solution already containing the surfactant and suitable for immediate administration. An example of a therapeutic agent for which such a system is preferred is propofol, which may be presented in a liquid form with the preferred surfactant in a clear colorless solution, and is administered directly without further dilution. Extemporaneous injection solutions and suspensions may be prepared from sterile powder, granules, tablets, etc.

The formulations may be prepared by the general methods and examples presented below, and additional methods known to those of ordinary skill in the art, for example by means of conventional mixing, dissolving, emulsifying, spray drying, or lyophilizing processes. Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Examples section. Reaction progress may be monitored by conventional methods such as thin layer chromatography (TLC). Intermediates and products may be purified by methods known in the art, including column chromatography, HPLC or recrystallization.

In a preferred embodiment, the therapeutic agent is lyophilized, and is later reconstituted and then diluted to a formulation for administration to a patient. Lyophilization is a freeze drying process that is often used in the preparation of pharmaceutical products to preserve their biological activity. A liquid composition is prepared, comprising the therapeutic agent in a solvent, and preferably further comprising a bulking agent. Preferably, the solvent comprises up to about 98 percent tert-butyl alcohol, with the remainder water. In a preferred embodiment, the bulking agent is mannitol and the solvent is a 60:40 mix of tert-butyl alcohol and water. In another preferred embodiment, the bulking agent is poloxamer 188 and the solvent is a mix ranging from 50:50 to 98:2, and preferably about 95:5, tert-butyl alcohol and water.

The liquid composition is then lyophilized to form a dry cake-like product. The process generally involves drying a previously frozen sample in a vacuum to remove the ice, leaving the non-water components intact, in the form of a powdery or cake-like substance. Any appropriate drying parameters may be used. In an exemplary embodiment, the following drying parameters are preferred: a primary drying phase temperature of about −40° C. to 0° C. and pressure between best vacuum to about 200 mTorr; and a secondary drying phase at temperatures up to 35° C., and pressure between best vacuum to about 200 mTorr. Any suitable solvent can be used for the lyophilization process, including, but not limited to, tert-butyl alcohol/water, DMSO, n-methylpyrrolidone, etc.

The lyophilized product can be stored for prolonged periods of time, and at elevated temperatures, without loss of biological activity, and can be readily reconstituted into a solution by the addition of an appropriate diluent containing the preferred surfactant. The advantage of lyophilization is that the water content is reduced to a level that greatly reduces the various molecular events which lead to instability of the product upon long-term storage. The lyophilized product is also more readily able to withstand the physical stresses of shipping. The lyophilized product is rehydrated at the time of use in a diluent to yield a particle-free solution for either direct administration or further dilution to an administrative solution.

An appropriate diluent can be any liquid which is biologically acceptable and in which the lyophilized powder is completely soluble. In a preferred embodiment, the diluent is a solution of sugar-based esters or ethers in sterile water (e.g., Water for Injection, USP), normal saline, D5W, or other aqueous carrier. Alcohol, e.g., ethanol, or other excipients may be included in the diluent.

The lyophilized product and the diluent are prepared and stored separately. The lyophilized product is reconstituted for administration to a patient by adding a diluent to the lyophilized product. The reconstituted solution may be administered directly or may be further diluted prior to administration. The reconstituted solution or the administration solution so formed may be preferably used immediately or within a short time of being formed, e.g., within 8 hours. Alternatively, the lyophilized product and a predetermined amount of diluent may be loaded each into separate chambers of a double-chamber vial system and only mixed immediately prior to administration to a patient. The amount of diluent used in admixture with the lyophilized product to form an administration solution may be chosen so as to obtain a desired concentration of therapeutic agent in the administration solution. The amount of diluent used is also chosen so that the solution is stable long enough to be administered.

Administration

The administration of the parenteral formulations may be for a prophylactic or therapeutic purpose, or alternatively can be used for diagnostic purposes. Preferred subjects for treatment include animals, most preferably *mammalian* species such as humans, and domestic animals such as dogs, cats and the like, subject to disease and other pathological conditions. A "patient" refers to a subject, preferably mammalian (including human).

Administration of the formulations is parenterally, preferably by injection or infusion, although implantation may be suitable for certain therapeutic purposes. Preferred routes of administration include intravenous, intraarterial, intramuscular, intracardiac, intracutaneous, subcutaneous, intraosseous, intradermal, intrathecal, intraperitoneal, intra-articular, intrasynovial, intracavernous, and other suitable routes for parenteral administration. In one preferred embodiment, the administration is intravenous, and in another preferred embodiment, the administration is intraperitoneal.

The dosage schedule and amounts effective for therapeutic and prophylactic uses, i.e., the "dosing regimen", will depend upon a variety of factors, including the stage of the disease or condition, the severity of the disease or condition, the general state of the patient's health, the patient's physical status, age and the like. In calculating the dosage regimen for a patient, the mode of administration also is taken into consideration. The dosage regimen also takes into consideration pharmacokinetics parameters well known in the art, i.e., the rate of absorption, bioavailability, metabolism, clearance, and the like. The state of the art allows the clinician to determine the dosage regimen for each individual patient, therapeutic agent and disease or condition treated. Single or multiple administrations of the parenteral formulations can be administered depending on the dosage and frequency as required and tolerated by the patient. For example, for some therapeutic agents it is essential that steady-state plasma levels are maintained, and thus the formulations may be administered by continuous infusion over 24 hours or optionally several days in order to maintain a steady-state plasma level.

Generally, the parenteral formulations may be administered in an amount which is therapeutically effective either as a single agent, or as combined with other treatments known to a skilled person such as radiation, or administered as part of a combination therapy comprising at least one other therapeutic agent. The administration of a combination of active agents may be simultaneous or consecutive, with either one of the active agents being administered first. The dosage of the active agents of a combination treatment may depend on effectiveness and site of action of each active agent, as well as synergistic effects between the agents used for combination therapy.

In another embodiment, the invention provides a method of administering a therapeutic agent to a subject in need of treatment which comprises administering a parenteral formulation to a subject in need of such treatment. More specifically, such a method of administering a therapeutic agent comprises: (a) diluting a pharmaceutical formulation according to the invention, e.g., in the form of an infusion or lyophilization concentrate, with a diluent containing sugar-based esters or ethers, to form a parenteral formulation suitable for parenteral administration; and (b) administering such parenteral formulation to the subject. The method may further comprise diluting the parenteral formulation with a sterile liquid carrier, for example, Water for Injection, normal saline, or D5W, prior to administration.

In another embodiment, the invention provides a method of treating cancer in a patient in need of such treatment, comprising administering a therapeutically effective amount of a pharmaceutical composition comprising docetaxel or a pharmaceutically acceptable salt thereof, and a sugar-based surfactant selected from the group consisting of sugar fatty acid esters, sugar fatty alcohol esters, and sugar fatty alcohol ethers. Also contemplated is the use of sugar-based esters or ethers in the manufacture of a medicament suitable for parenteral administration.

Application of the teachings of the present invention to a specific problem or environment is within the capabilities of one having ordinary skill in the art in light of the teachings contained herein. Examples of the products and processes of the present invention appear in the following examples.

Example 1

Docetaxel-Saline Formulations

Lyophilized docetaxel is reconstituted with a sucrose cocoate solution containing ethanol to prepare a clear intermediary solution. The clear intermediary solution is added to 0.09% sodium chloride to form an administrative formulation of between 0.3 and 0.74 mg/mL docetaxel.

Example 2

Docetaxel-5% Dextrose Formulations

Lyophilized docetaxel is reconstituted with a sucrose cocoate solution containing ethanol to prepare a clear intermediary solution. The clear intermediary solution is added to 5% Dextrose to form an administrative formulation of between 0.3 and 0.74 mg/mL docetaxel.

Example 3

Lyophilized Therapeutic Agent Formulations

Lyophilized therapeutic agents are obtained from commercial sources, for example lyophilized docetaxel is obtained from Sigma-Aldrich (St. Louis, Mo.). Alternatively, the therapeutic agent is obtained and then lyophilized. For example, the therapeutic agent (e.g., docetaxel) may be mixed with a bulking agent (e.g., mannitol or poloxamer 188), and optionally a cryoprotectant, and then dissolved in a suitable solvent, such as tert-butyl alcohol, which may be mixed with water. The solution is stirred gently at room temperature, filtered, e.g., through a 0.2 µm filter, filled into a vial, and then rapidly frozen and lyophilized, thereby obtaining a dry lyophilized cake.

Reconstitution solutions for rehydrating the cake are formulated comprising various concentrations (from 10 to 90%) of sucrose fatty acid esters in water, with and without ethanol. Ethanol is not necessary for the sucrose esters to exert their surface active properties. Solutions are made using one or more sucrose fatty acid esters, such as sucrose cocoate (Croda, Parsipanny, N.J.), sucrose stearate (Croda), sucrose laurate (Mitsubishi, Japan), and sucrose stearate (Mitsubishi). The solution is mixed at room temperature, the temperature is lowered to 17° C., and the solution is stored for a period of time (~2 hours) and filtered through a Depth Filter (1 µm to 0.2 µm) and then a 0.2 µm filter. The filtered solution is then filled into vials and sealed. This solution is suitable for use as a reconstituting diluent for lyophilized therapeutic agents such as docetaxel, paclitaxel, cyclosporine and etoposide and the like.

During reconstitution, the reconstitution solution is gently mixed with the lyophilized therapeutic agent cake. Minimal, if any, foaming occurs, and the foam dissipates quickly (~5 minutes post-mixing). An aliquot of the formulation is then transferred to the administration solvent (e.g., normal saline or D5W).

Example 4

Lyophilization of Docetaxel-Mannitol Formulations

A docetaxel formulation containing mannitol as a bulking agent was prepared. In an isolator, mannitol (0.055000 g; EMD Chemicals, Inc., Gibbstown, N.J.) was weighed and added to a Hicoflex® charge bag with a rinse port (GEA Process Engineering, Inc., Columbia, Md.). The mannitol was transferred to a stainless steel vessel containing Water for Injection, USP (q.s. to 1.0 mL) at 25-30° C., and mixed at 600-800 RPM until the mannitol was completely dissolved (about 10 minutes). Anhydrous docetaxel (0.016667 grams; AZAD Pharma Ltd., Pointe-Clare, Quebec, Canada) was added to a separate stainless steel vessel containing warm (50-60° C.) tert-butyl alcohol (q.s. to 1.0 mL; 96%; ACS grade; J. T. Baker, Phillipsburg, N.J.), and mixed at 800-1200 RPM until the docetaxel was completely dissolved and the solution was homogeneous (about 50 minutes). The vessel was tightly covered, and the docetaxel solution cooled to about 25-30° C. The mixing rate was then decreased to 600-800 RPM and temperature was maintained at 25-30° C.

An aliquot of the mannitol solution was added to the vessel containing the docetaxel solution, which was then re-sealed and mixed until homogeneous (about 15 minutes) at about 600-800 RPM. The mixed solution was then filtered, and a number of pre-sterilized lyophilization vials were aseptically filled with the filtered solution. The vials were immediately transferred to a freeze-dryer and lyophilized under vacuum using nitrogen. A lyophilizate was obtained, and used to reconstitute clear solutions with the sucrose fatty acid ester diluent. The clear solution was further diluted for administrative purposes in saline and D5W. Stability measurements indicated that the solutions remained clear and non-precipitated after 24 hours.

Example 5

Lyophilization of Docetaxel-Poloxamer 188 Formulations

A docetaxel formulation containing Poloxamer 188 as a bulking agent was prepared. In an isolator, anhydrous docetaxel (0.010000 grams; AZAD Pharma Ltd., Pointe-Clare, Quebec, Canada) was weighed and added to a Hicoflex® charge bag with a rinse port (GEA Process Engineering, Inc., Columbia, Md.). The docetaxel was transferred to a sealed stainless steel vessel containing warm (50-60° C.) tert-butyl alcohol (0.722936 g; density=0.7858). The solution was mixed at 800-1200 RPM until the docetaxel was completely dissolved (about 35 minutes). Tert-butyl alcohol (0.031432 g; density=0.7858; 96%; ACS grade; J. T. Baker, Phillipsburg, N.J.) was added to a sealed stainless steel wash vessel and maintained at a temperature above 30° C. The charge bag was re-attached to the isolator, and rinsed with tert-butyl alcohol from the wash vessel, into a stainless steel rinse vessel. The rinse was repeated twice more, with no more than half of the alcohol in the wash vessel used.

Poloxamer 188 (0.010000 grams; sold as Lutrol® F 68 by BASF, Florham Park, N.J.) was transferred to the vessel containing the docetaxel, and the vessel was resealed and mixed at 800-1200 RPM until the poloxamer was completely dissolved (about 35 minutes). The vessel was cooled to about 30-35° C., and stirring was then decreased to 400-600 RPM. The container used to transfer the poloxamer was rinsed with tert-butyl alcohol from the wash vessel, into the rinse vessel. The rinse was repeated twice more, and used all of the alcohol remaining in the wash vessel. The rinse vessel was then emptied.

Water for Injection, USP (0.040000 grams) was added to the rinse vessel. Half of the water in the rinse vessel was used to rinse the wash vessel. The rinse was transferred into the charge bag and then into the vessel containing the docetaxel-poloxamer solution. The remaining contents of the rinse vessel were used to rinse the wash vessel. The rinse was transferred into the container used to transfer the poloxamer, and then into the vessel containing the docetaxel-poloxamer solution. At this point the formulation was at final QS weight, or, if not, was adjusted to QS weight with Water for Injection, USP. The vessel was re-sealed, mixed until the solution was homogeneous (about 15 minutes), and then cooled to about 20-25° C.

The mixed solution was then filtered, and a number of pre-sterilized lyophilization vials were aseptically filled with the filtered solution. The vials were immediately transferred to a freeze-dryer and lyophilized under vacuum using nitrogen. A lyophilizate was obtained, and used to reconstitute clear solutions with the sucrose fatty acid ester diluent. The clear solution was further diluted for administrative purposes in saline and D5W. Stability measurements indicated that the solutions remained clear and non-precipitated after 24 hours.

Example 6

Docetaxel-Mannitol Formulations

Lyophilization is performed to yield vials containing lyophilized cake comprising docetaxel and mannitol in a ratio of 1:1.5 to 1:3, preferably 1:1.8 to 1:2.7, more preferably 1:2.0 to 1:2.5, and most preferably 1:2.2. The amount of cake may vary, for example a 1:2.2 ratio may be obtained by a vial comprising 20 mg docetaxel and 44 mg mannitol, a vial comprising 80 mg docetaxel and 176 mg mannitol, or a vial comprising 120 mg docetaxel and 264 mg mannitol.

Reconstitution solutions (diluent) for rehydrating the cake may contain varying amounts of sugar surfactant in water, with and without an alcohol such as ethanol. Preferably, the diluent comprises 25-40% sugar surfactant, 15-30% alcohol (if used), and the remainder water (all w/w), and preferably comprises 30-35% sugar surfactant, 20-25% alcohol, and the remainder water, and more preferably comprises about 31.5% sugar surfactant, about 22.5% alcohol, and the remainder (about 46%) water. Most preferably, the diluent comprises about 31.6% w/w sucrose cocoate (Croda, Parsipanny, N.J.), 22.5% w/w ethanol, and 45.9% water. The amount of diluent used may vary, for example, three diluent vials corresponding to the three lyo vials described above may contain 2 mL, 8 mL, and 12 mL of diluent, respectively.

Example 7

Docetaxel-Poloxamer 188 Formulations

Lyophilization is performed to yield vials containing lyophilized cake comprising docetaxel and poloxamer 188 in a ratio of 1:1 to 1:5, preferably 1:2 to 1:4, more preferably 1:2.5 to 1:3.5, and most preferably 1:3. The amount of cake may vary, for example a 1:3 ratio may be obtained by a vial comprising 10 mg docetaxel and 30 mg poloxamer 188, a vial comprising 20 mg docetaxel and 60 mg poloxamer 188, a vial comprising 80 mg docetaxel and 240 mg poloxamer 188, or a vial comprising 120 mg docetaxel and 360 mg poloxamer 188.

Reconstitution solutions (diluent) for rehydrating the cake may contain varying amounts of sugar surfactant in water, with and without an alcohol such as ethanol. Preferably, the diluent comprises 25-40% sugar surfactant, 15-30% alcohol (if used), and the remainder water (all w/w), and preferably comprises 30-35% sugar surfactant, 20-25% alcohol, and the remainder water, and more preferably comprises about 31.5% sugar surfactant, about 22.5% alcohol, and the remainder (about 46%) water. Most preferably, the diluent comprises about 31.6% w/w sucrose cocoate (Croda, Parsipanny, N.J.), 22.5% w/w ethanol, and 45.9% water. The amount of diluent used may vary, for example, four diluent vials corresponding to the four lyo vials described above may contain 1 mL, 2 mL, 8 mL, and 12 mL of diluent, respectively.

Example 8

Propofol Formulations

Propofol Injection can be prepared as a liquid formulation such that the Propofol content in the formulation is 200 mg/mL. The method transfers the appropriate amount of Propofol, 295.3 mg, to a 20 mL container vessel containing approximately 10.0 mL of 5% Dextrose. To this is added 4.0 mL of a sucrose cocoate solution. The sucrose cocoate solution contains 40% w/w sucrose cocoate solids, 7% w/w ethanol and 53% w/w water. The container is seal and the mixture is mixed until clear. The solution is then filtered through a 0.2 micron filter. Addition of Benzyl alcohol or other antimicrobials may be added to the formulation.

Example 9

Cyclosporine Formulations

The method transfers 520.1 mg of cyclosporine into a 20 mL container. To this is added 10.0 mL of a sucrose cocoate solution. The sucrose cocoate solution contains 40% w/w sucrose cocoate solids, 7% w/w ethanol and 53% w/w water. The formulation is mixed until a clear solution is formed. The solution is then further diluted to the administrative dose concentration of 0.5 mg/mL in 0.9% Saline or 5% Dextrose. A clear solution is obtained.

Example 10

Etoposide Formulations

The method transfers 221.8 mg of etoposide into a 20 mL container. To this is added 7.0 mL of the sucrose laurate, from Mitsubishi Kagaku, 3 mL ethanol, 0.3 mL Benzyl Alcohol and 20 mg Citric Acid. The solution was mixed until fully dissolved. The solution is filtered and then further diluted to the administrative dose concentration of about 2 mg/mL in 0.9% Saline or 5% Dextrose. A clear solution is obtained.

The above description, drawings and examples are only illustrative of preferred embodiments which achieve the objects, features and advantages of the present invention. It is not intended that the present invention be limited to the illustrative embodiments. Any modification of the present invention which comes within the spirit and scope of the claims should be considered part of the present invention.

What is claimed is:

1. A pharmaceutical solution for injection or infusion administration comprising a therapeutic agent selected from the group consisting of taxanes, antineoplastics, anaesthetics, steroids and antibiotics and sucrose cocoate.

2. The composition of claim 1, wherein the therapeutic agent is poorly soluble in water.

3. The composition of claim 1, wherein the composition further comprises a bulking agent.

4. The composition of claim 1, wherein the composition further comprises a tonicity agent.

5. The composition of claim 1, wherein the composition further comprises a preservative.

6. The composition of claim 1, the therapeutic agent being a taxane.

7. The composition of claim 6, the therapeutic agent being docetaxel.

8. The composition of claim 1, the therapeutic agent being an anaesthetic.

9. The composition of claim 1, the therapeutic agent being a steroid.

10. The composition of claim 1, the therapeutic agent being an antibiotic.

\* \* \* \* \*